(12) United States Patent
Freudiger

(10) Patent No.: US 8,414,618 B2
(45) Date of Patent: Apr. 9, 2013

(54) ELASTIC STABILIZATION SYSTEM FOR VERTEBRAL COLUMNS

(75) Inventor: Stefan Freudiger, Bremgarten (CH)

(73) Assignee: Spinelab AG, Zug (CH)

( * ) Notice: Subject to any disclaimer, the term of this patent is extended or adjusted under 35 U.S.C. 154(b) by 1549 days.

(21) Appl. No.: 11/514,240

(22) Filed: Sep. 1, 2006

(65) Prior Publication Data
US 2007/0016201 A1    Jan. 18, 2007

Related U.S. Application Data

(62) Division of application No. 10/442,141, filed on May 21, 2003, now Pat. No. 7,125,410.

(30) Foreign Application Priority Data

May 21, 2002    (CH) .................................... 0853/02

(51) Int. Cl.
*A61B 17/70* (2006.01)
(52) U.S. Cl. .................................................. 606/254
(58) Field of Classification Search .................. 606/246, 606/250–257
See application file for complete search history.

(56) References Cited

U.S. PATENT DOCUMENTS

| | | | |
|---|---|---|---|
| 4,041,939 A * | 8/1977 | Hall | 606/254 |
| 4,697,582 A * | 10/1987 | William | 606/254 |
| 4,719,905 A | 1/1988 | Steffee | 606/61 |
| 4,773,402 A * | 9/1988 | Asher et al. | 606/250 |
| 5,030,220 A * | 7/1991 | Howland | 606/261 |
| 5,282,863 A | 2/1994 | Burton | 623/17 |
| 5,658,286 A | 8/1997 | Sava | 606/61 |
| 5,662,651 A | 9/1997 | Tornier et al. | 606/60 |
| 6,368,319 B1 * | 4/2002 | Schaefer | 606/60 |
| 6,623,484 B2 | 9/2003 | Betz et al. | 606/61 |
| 6,783,527 B2 * | 8/2004 | Drewry et al. | 606/254 |
| 2003/0083657 A1 | 5/2003 | Drewry et al. | 606/61 |
| 2003/0187434 A1 * | 10/2003 | Lin | 606/61 |
| 2005/0010216 A1 | 1/2005 | Gradel et al. | 606/61 |

FOREIGN PATENT DOCUMENTS

| | | |
|---|---|---|
| EP | 0498709 A1 | 8/1992 |
| EP | 0516567 A1 | 12/1992 |
| EP | 0667127 A1 | 8/1995 |
| EP | 0669109 A1 | 8/1995 |
| EP | 0634911 B1 | 10/1997 |
| WO | WO01/45576 | 6/2001 |

* cited by examiner

*Primary Examiner* — Kevin T Truong
*Assistant Examiner* — Michael Araj
(74) *Attorney, Agent, or Firm* — Jacobson Holman PLLC

(57) ABSTRACT

A vertebral column implant for the elastic stabilization of motion segments including an elastically bendable connecting element which can be passed through the seats of a number of pedicle screws having offset seat axes and be anchored. The connecting element is bendable elastically about every axis of its cross-section in such a way that the connecting element can be passed through, or inserted in, the seats of the screwheads, one behind the other, even when the seats are not situated on one and the same axis.

26 Claims, 4 Drawing Sheets

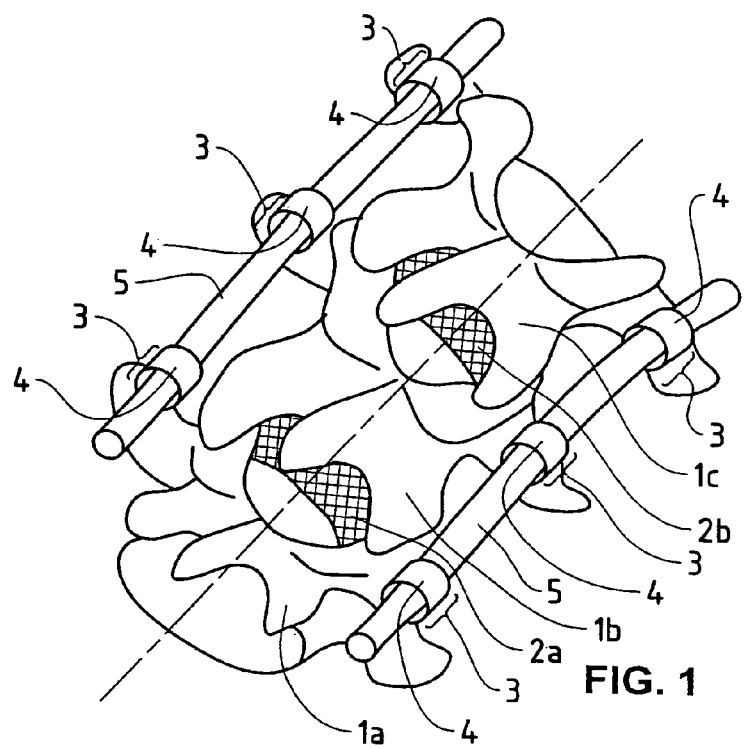
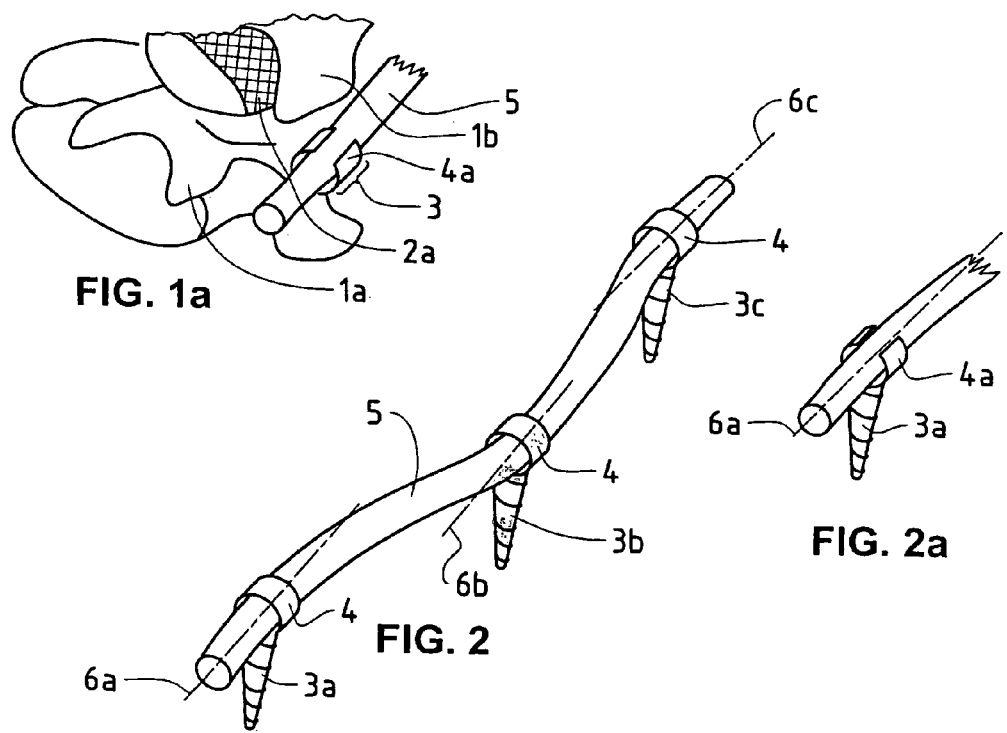

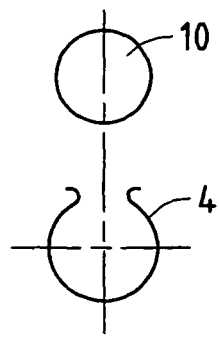 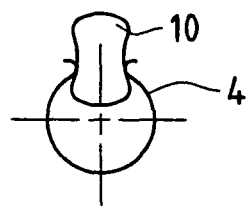 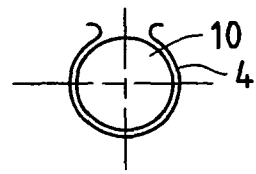
FIG. 6a     FIG. 6b     FIG. 6c
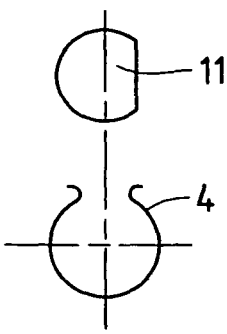 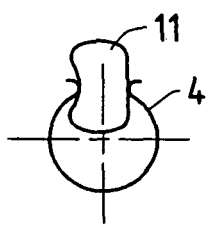 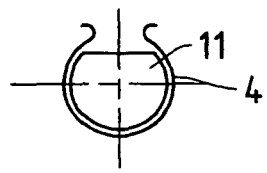
FIG. 7a     FIG. 7b     FIG. 7c
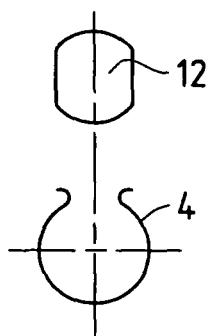 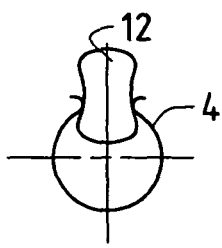 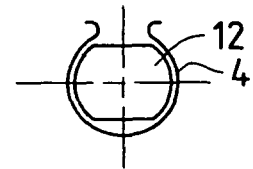
FIG. 8a     FIG. 8b     FIG. 8c

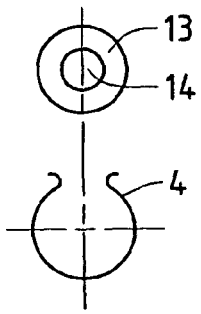 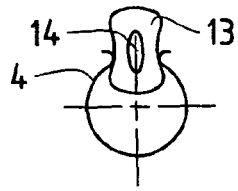 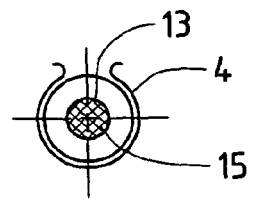
FIG. 9a   FIG. 9b   FIG. 9c
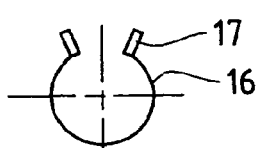 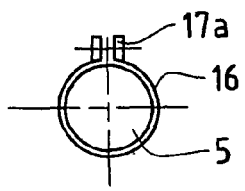
FIG. 10a   FIG. 10b
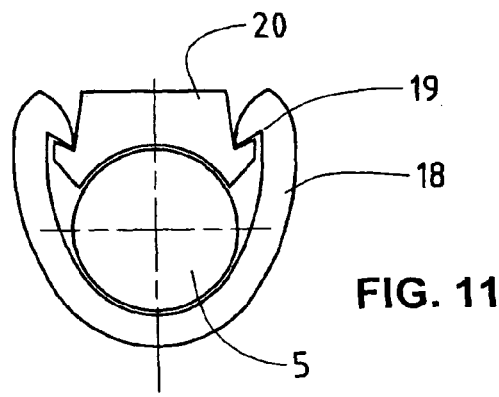
FIG. 11
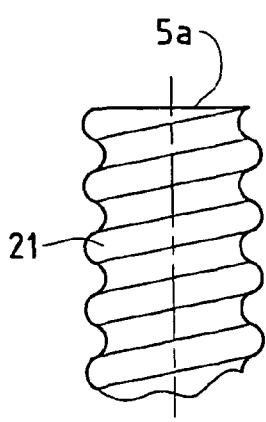 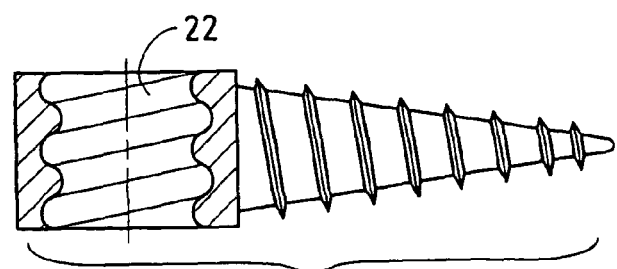
FIG. 12a   FIG. 12b

ELASTIC STABILIZATION SYSTEM FOR VERTEBRAL COLUMNS

This is a divisional application of application Ser. No. 10/442,141, filed May 21, 2003, now U.S. Pat. No. 7,125,410.

FIELD OF THE INVENTION

The present invention relates to a vertebral column implant of the type comprising a connecting element and a number of bone screws, each having a seat for this connecting element. The implant serves to elastically stabilize the vertebral column of a person having severe back pain.

BACKGROUND OF THE INVENTION

The current prior art still comprises mostly stabilization systems aimed at an osseous fusion (stiffening) of affected vertebrae. Elastic systems which merely support and stabilize segments of the vertebral column, but are not supposed to fuse it, have appeared only sporadically so far. These recent elastic systems still involve considerable implant time and expenditure. For reasons of production costs, operating time, and security in handling, future vertebral column stabilization systems should be as simple as possible.

The advantages of elastic stabilizations are becoming increasingly well known, above all by young patients, so that various inventors have developed and disclosed such systems. However, these inventions involve drawbacks which will be explained with the aid of the following examples.

Although the invention according to patent EP 0498 709 B1 to Graf intends to stabilize elastically, it has the drawback that the system works only in flexion (tension) but not in extension (compression). The stabilization is usually produced by means of at least two individual, mutually offset textile loops.

The invention according to patent application WO 93/20771 of Mazel also intends to connect vertebrae by means of pairs of flexible longitudinal rods. However, this invention has the drawbacks that the longitudinal rods have hardly any resistance to buckling and therefore can hardly transmit compressive forces, that the flexibility of the rods disposed in pairs cannot be the same in all directions, and that the transmission of force to the bone screws must take place by means of numerous components.

The invention according to patent EP 0516 567 B1 to Navas proposes the insertion of shock absorbers between the vertebrae. This invention has the drawbacks, however, that these shock absorbers are not longitudinally adjustable and that the plastic material is passed through a narrow place (neck), which results in a considerable decrease in strength.

The invention according to U.S. Pat. No. 5,282,863 A to Burton also intends to stabilize flexibly. However, this invention has the drawbacks that the system is too wide and can be put in place posteriorly only if the pedicles are removed, that it can be used for only one segment, that it cannot, for example, be passed through three screws lying one behind the other and offset, that the bore in the connecting element results in considerable weakening, and that the oval cross-section of the connecting element has only minimum shear strength and minimum resistance to buckling in the anterior/posterior direction.

Furthermore, for fastening the connecting element to the pedicle screw, a locking cap must be used, which is a disadvantage during the operation.

The invention according to patent application EP 0 667 127 A1 of Sanders seeks to achieve a certain elasticity by means of a metallic connection in that the form of the connection part allows local bending. However, this invention has the drawback that the connecting parts are not longitudinally adjustable and cannot be inserted multisegmentally.

The invention according to patent EP 0669 109 B1 to Baumgartner et al. likewise intends to stabilize adjacent vertebral segments elastically by using a cord for tensile forces and a plastic cushion for compressive forces. This invention has the drawbacks, however, that the system contains an expensive cord band, any desired cushion heights can be achieved only by means of a plurality of standard cushions, variation of the preload on the cord leads to conditions not reproducible biomechanically, and implantation is relatively expensive and takes a long time.

SUMMARY OF THE INVENTION

Accordingly, the tasks underlying the present invention are to transmit both tensile and compressive forces between adjacent vertebrae by means of one and the same connecting element and to be passed through bone screws, preferably anchored in the pedicles, or to be insertable in such screws, which by their nature do not lie on one axis.

The solution to this task is distinguished in that an elastic connecting element is used which, owing to the local, maximally allowable cross-sections, achieves sufficient shear strength, tensile strength, compressive strength, and resistance to buckling to transmit the forces to be expected lastingly and reliably.

Consequently, the subject of the invention is a vertebral column implant comprising a connecting element and a number of bone screws, each having a seat for this connecting element, which is characterized in that the connecting element is bendable elastically about every axis of its cross-section in such a way that it can be passed through or inserted in the seats of a number of screwheads one behind the other even when the latter are not situated on one and the same axis.

The connecting element bendable elastically about every axis of its cross-section is made of an elastically bendable biocompatible material, preferably a plastic. Such a plastic is a polymer which may be composed of the same or different components and has the desired mechanical and chemical properties, e.g., a polyurethane-based material such as aromatic polycarbonate-polyurethanes (suitable commercially available products are, for example: BIONATE® of Polymer Technology Group, 2810 7th Street, Berkeley, Calif. 94710, U.S.A., and ChronoFlex®C of CardioTech International Inc., 78E Olympia Ave., Woburn, Mass. 01801-2057, U.S.A.). The connecting element proposed according to the invention has sufficient bending elasticity about all axes of its cross-section, so that the insertion thereof is made possible even in seats of screwheads which are not on one axis but rather lie on a line running arbitrarily, or are, by their nature owing to differing arrangements of vertebrae, offset in different directions.

The connecting element with the stabilizing effect may have a cross-section varied in the direction of the rod axis so that it has a stiffness variable dependent upon position, giving it a locally adapted stabilization effect. The stabilization effect of adjacent vertebrae may thereby be adjusted up to local stiffening with gradual transitions. For this purpose, the connecting element may take the form of a hollow rod with walls of varied thickness. When the following text speaks of "original cross-section" in connection with the connecting element, this means that the cross-section corresponds essentially to the original cross-section existing prior to insertion of the element, which does not exclude the occurrence of deviations, e.g., through compression or through bias by the fastening means disposed on the screwhead.

The seats which are integrated in the heads of the bone screws preferably have a C-shaped form in which the elastic connecting element can be engaged in the correct position by the surgeon. For this purpose the seat may be designed in such a way that it is likewise elastic to a certain extent. Thereby, during the operation, fastening without additional small implant parts is made possible.

For the purpose of fixing the connecting elements to the seats, their surfaces, which come into contact with each other at the time of fixing, may be provided with an interlocking-surface structure so that when a connecting element is engaged in a seat, mutual shifting is no longer possible. This surface structure is, for example, a suitable grooved structure having grooves at right angles to the connecting element. The grooved structure may also be a threaded structure making screwing-in possible. Other interengageable surface structures may also be chosen, such as a nub-and-depression structure, for instance. When a grooved structure at right angles to the longitudinal axis of the connecting element is used, the grooved structure in the seat may be so designed that engagement of the grooved structure of the connecting element in an extended grooved structure in the insertion opening of the seat is possible. In this way, pre-fixing can be achieved so that prior to engagement of the connecting element in the seat, the surgeon may check its anatomically correct position.

The vertebral column implant according to the present invention is capable of stabilizing vertebral columns which have become unstable due to degenerative or iatrogenic processes and thus painful, and of reducing or completely avoiding pain. The advantage of an elastic stabilization is above all that individual vertebrae need no longer be fused as previously, which led in many cases to secondary damage to adjacent segments. The particular advantage of the present invention resides in the low production costs, as well as in the simple and safe implantation technique of the system.

BRIEF DESCRIPTION OF THE DRAWINGS

The following list of figures gives an overall view of the accompanying drawings.

Shown diagrammatically are:

FIG. 1, a vertebral column segment having a number of vertebrae with left and right pedicle screws and a left and right elastically bendable connecting rod;

FIG. 1a, a partial view of a vertebral column segment, but with an alternative seat in the head of the pedicle screws;

FIG. 2, by way of example, three pedicle screws having mutually offset axes and the inserted elastically bendable connecting rod;

FIG. 2a, a partial view of FIG. 2 with an alternative pedicle screw;

FIG. 6a, the seat with slot in the screwhead and the rod outside the seat; FIG. 6b, the elastically compressed rod upon insertion into the seat with slot in the screwhead; FIG. 6c, the elastic rod in its original cross-section in the seat with slot;

FIG. 7a, the seat with slot in the screwhead and the rod with a flattened side outside the seat; FIG. 7b, the elastically compressed rod with a flattened side upon insertion into the seat with slot in the screwhead; FIG. 7c, the elastic rod with a flattened side in its original cross-section rotated in the seat with slot;

FIG. 8a, the seat with slot in the screwhead and the rod with two parallel flattened sides outside the seat; FIG. 8b, the elastically compressed rod with two parallel flattened sides upon insertion in the seat with slot in the screwhead;

FIG. 8c, the elastic rod with two parallel flattened sides in its original cross-section rotated in the seat with slot;

FIG. 9a, the seat with slot in the screwhead and the rod with a hollow space in the center outside the seat; FIG. 9b, the elastically compressed rod with a hollow space in the center upon insertion into the seat with slot in the screwhead;

FIG. 9c, the elastic rod with a hollow space in the center in its original cross-section with a filler in the hollow space in the seat with slot;

FIG. 10a, the seat with slot with a clamp device; FIG. 10b, the elastic rod clamped in the seat with slot;

FIG. 11, the seat with slot with a hook device and a hooked-in wedge;

FIG. 12a, an elastically bendable connecting rod having a grooved surface provided with a pitch; FIG. 12b, the grooved seat, provided with the same pitch, in the head of the pedicle screw.

DETAILED DESCRIPTION OF THE PREFERRED EMBODIMENTS

Figure 3:
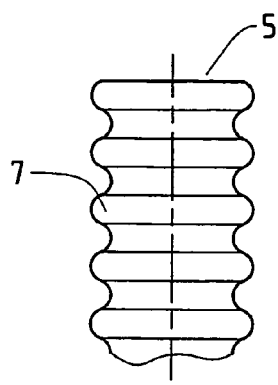
FIG. 3, a partial view of an elastically bendable connecting rod having a grooved surface.

The present invention is described in more detail below with reference to the accompanying drawings, which merely represent examples of embodiments.

FIG. 1 shows a vertebral column segment having three vertebrae 1a, 1b, 1c, and two discs 2a, 2b situated between them. Inserted to the left and right of each vertebra is a pedicle screw 3, each having a seat 4 in each of which an elastically bendable, rod-shaped connecting element 5 is fastened to the left and right. The connecting elements 5 are mounted in the seats 4 and serve for flexible stabilization of the vertebrae.

FIG. 1a is a partial view of an analogous vertebral column segment having a pedicle screw 3 with an open seat 4a for mounting a connecting element 5.

FIG. 2 shows three pedicle screws 3a, 3b, 3c having mutually offset axes (6a, 6b, 6c) of their seats in the head and the inserted elastically bendable, rod-shaped connecting element 5.

FIG. 2a shows a partial view corresponding to FIG. 2, but with an open seat 4a for the connecting element 5.

FIG. 3 shows a partial view of an elastically bendable, rod-shaped connecting element 5 with a grooved surface 7. The grooving corresponding to the connecting rod serves for a form-engagement in a correspondingly designed seat of a pedicle screw.

Figure 4:
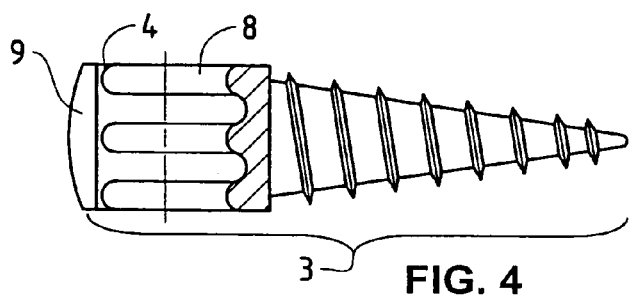
FIGS. 4 and 4a, views of a pedicle screw having a grooved seat in the head.
Figure 4A:
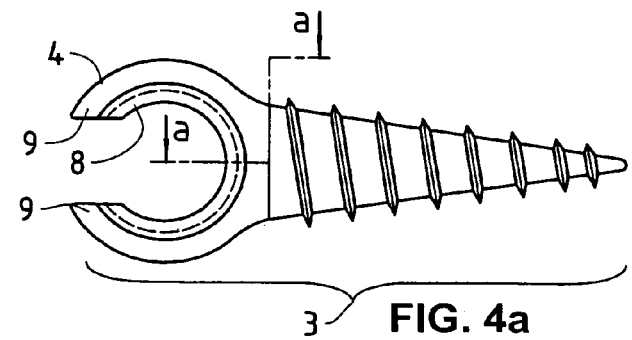

FIG. 4 shows the side view of a pedicle screw 3a, the head of which is shown as a partial section (plane a-a in FIG. 4a). The head is designed as seat 4 having an inner grooved surface with ribs 8. Provided on both sides in the seat opening are bevels 9 which facilitate the insertion of a stabilization element. FIG. 4a shows the top view of the same pedicle screw. Seen here is the opening of the seat 4 with the two bevels 9 and a rib 8 of the inner grooved surface.

Figure 5:
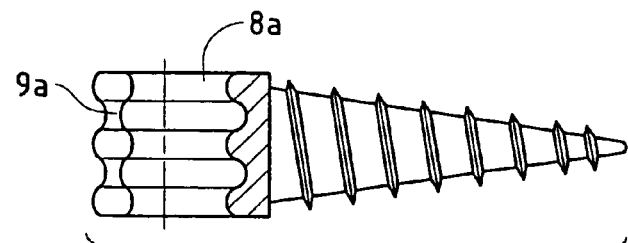
FIGS. 5 and 5a, views of a pedicle screw having a grooved seat in the head, where the grooved structure is extended into the slot of the seat and the bevel projecting beyond it.
Figure 5A:
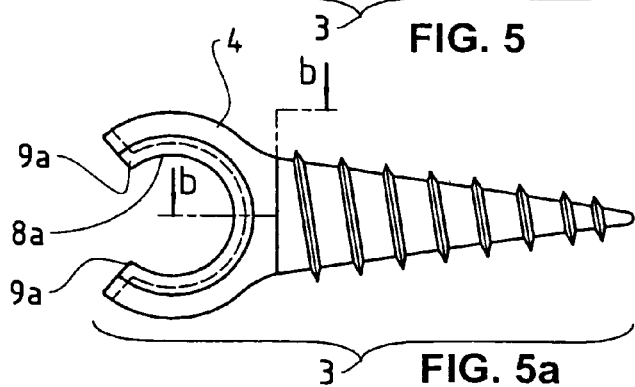

FIG. 5 is the side view of a further embodiment of a pedicle screw 3, the head of which, also shown as a partial section (taken on the line b-b of FIG. 5a), is designed as a modified seat 4. The seat has in the slot thereof a grooved surface with ribs 8a which extend into the bevel 9a. By means of this design of the seat, a correspondingly grooved connecting element can be prepositioned without slipping prior to snapping into the seat so that the surgeon can check the correct position. FIG. 5a shows the top view of same pedicle screw. Seen here is the opening of the seat 4 with the two bevels 9a and a rib 8a of the inner grooved surface. Seen here is the extension of the grooved surface to the bevel 9a.

FIG. 6a shows diagrammatically in section a seat 4 with slot in the screwhead of a pedicle screw and a connecting element 10 which is still situated outside the seat. FIG. 6b shows the elastically compressed connecting element 10 during insertion in the slot of the seat 4 in the screwhead. FIG. 6c shows in section the elastic connecting element 10 again in its original cross-section, introduced into the seat 4 with slot in the screwhead.

FIG. 7a shows in section the screwhead designed as seat 4 with slot and the rod-shaped connecting element 11 with a flattened side still outside the seat 4. FIG. 7b shows the elastically compressed connecting element 11 with a flattened side upon insertion into the seat with slot in the screwhead. FIG. 7c shows the elastic connecting element 11 with a flattened side again in its original cross-section, introduced into the seat 4 with slot in the screwhead, rotated by 90°.

FIG. 8a shows in section the seat 4 with slot in the screwhead and the connecting element 12 with two parallel flattened sides still outside the seat 4. FIG. 8b shows the elastically compressed connecting element with two parallel flattened sides 12 upon insertion in the seat 4 with slot in the screwhead. FIG. 8c shows the elastic connecting element 12 with two parallel flattened sides again in its original cross-section introduced into the seat 4 with slot in the screwhead, rotated by 90°.

FIG. 9a shows in section the seat 4 with slot in the screwhead and a connecting element 13 with a hollow space 14 in the center still outside the seat 4. FIG. 9b shows the elastically compressed connecting element 13 with a hollow space 14 in the center upon insertion into the seat 4 with slot in the screwhead. Here the hollow space 14 in the center of the connecting element 13 facilitates the elastic compression of the connecting element for easier insertion. FIG. 9c shows the elastic connecting element 13 with a hollow space 14 in the center again in its original cross-section, introduced into the seat 4 with slot in the screwhead, but now provided (optionally) with a plug 15 filling the hollow space, and form-lockingly anchored with the aid of the grooved surfaces disposed in the seat 4 and on the connecting element 13.

FIG. 10a shows in section a further embodiment of a seat 16 with slot in the screwhead provided with a clamp device 17. FIG. 10b shows the seat 16 with slot in the screwhead, an inserted connecting element 5 in its clamped cross-section and with clamp device 17 pulled together.

FIG. 11 shows a further embodiment of a seat 18 with slot in the screwhead, provided with a hook device 19 and a wedge 20, hooked in under preload, for holding the connecting element 5.

FIG. 12a shows a partial view of an elastically bendable, rod-shaped connecting element 5a with grooved surface provided with a pitch 21, and FIG. 12b shows the grooved seat in the head of the pedicle screw 3 provided with the same pitch. The grooves with pitch cause the rod to act like a screw and the seat in the screwhead to act like a nut, so that the rod can be screwed into the screwheads by rotation about the longitudinal axis and passed through.

The invention claimed is:
1. A vertebral column implant comprising
a connecting element and a plurality of bone screws,
each bone screw having a seat in a screwhead for the connecting element,
the seat of the screwhead of each of the plurality of bone screws fixing the connecting element in the seat,
segments of the connecting element between adjacent seats being fastened in place by the adjacent seats and having bending elasticity between adjacent vertebrae for flexible elastic stabilization of the segments between adjacent vertebrae,
the connecting element being made of an elastic material, bendable elastically about every axis of its cross-section in such a way that the connecting element is passed longitudinally through, or inserted in, the seats of the screwheads, one behind the other, even when the seats are not situated on one and the same axis and the connecting element elastically stabilizing a vertebral column of a person having severe back pain by elastic adjustment of the connecting element of both tensile and compressive forces between successive bone screws.

2. The vertebral column implant according to claim 1, wherein the elastic material consists of a biocompatible plastic composed of one or more kinds of monomer components.

3. The vertebral column implant according to claim 2, wherein the biocompatible plastic is a plastic on the basis of polyurethane.

4. The vertebral column implant according to claim 1, wherein the elastic connecting element has a structure with one or more hollow spaces.

5. The vertebral column implant according to claim 4, wherein the elastic connecting element has a tubular cross-section with a wall thickness variable along the connecting element, the wall thickness conferring a desired variable stiffness upon the connecting element according to a position.

6. The vertebral column implant according to claim 1, wherein the seat of the screwhead has a slot so that the connecting element is inserted and anchored in the seat with elastic deformation.

7. The vertebral column implant according to claim 1, wherein a grooved structure of the seat of the screwhead is continued into a plurality of bevels of the slot so that the elastic connecting element is pre-positioned for verifying a correct spacing of the vertebrae.

8. The vertebral column implant according to claim 1, wherein the connecting element has a round cross-section with a flat side so that the connecting element is introduced into the seat with a reduced inside width and thereafter anchored by a rotation.

9. The vertebral column implant according to claim 1, wherein the connecting element has a round cross-section with two parallel flat sides so that the connecting element is introduced into the seat with a reduced inside width and thereafter anchored by a rotation.

10. The vertebral column implant according to claim 1, wherein the connecting element has a hollow space about the longitudinal axis, the hollow space facilitating elastic deformation for introduction into the seat.

11. The vertebral column implant according to claim 10, further comprising a plug which is pushed into the hollow space after introduction of the connecting element into the seat.

12. The vertebral column implant according to claim 1, wherein the seat of the screwhead is clampable, and the connecting element is clamped after introduction.

13. The vertebral column implant according to claim 1, wherein the seat of the screwhead has a hook device into which a wedge is hooked with preload of the connecting element.

14. The vertebral column implant according to claim 1, wherein a structured surface of the seat and a structured surface of the connecting element each has annular grooves with channels of the grooves substantially at angles that are not a right angle to the longitudinal axis of the connecting element; and the grooves on the connecting element have a pitch, the seat on the screwhead has the same grooves with pitch and thus acts as a nut, so that the connecting element is screwed in and passed through the screwheads by rotation about the longitudinal axis.

15. A vertebral column implant comprising a connecting element and a number of bone screws, each of the bone screws having a seat for the connecting element, the seat of the screwhead of each of the number of bone screws fixing the connecting element in the seat, segments of the connecting element between adjacent seats being fastened in place by the adjacent seats and having bending elasticity between adjacent vertebrae for flexible elastic stabilization of the segments between adjacent vertebrae, the connecting element being made of an elastic material, bendable elastically about every axis of its cross-section in such a way that the connecting element is passed through or inserted in the seats of a number of screwheads one behind the other even when the screwheads are not situated on one and the same axis and the connecting element elastically stabilizing a vertebral column of a person having severe back pain by elastic adjustment of the connecting element of both tensile and compressive forces between successive bone screws.

16. The vertebral column implant according to claim 15, wherein the elastic material consists of a biocompatible plastic which is composed of one or more kinds of monomer components.

17. The vertebral column implant according to claim 16, wherein the biocompatible plastic is a plastic on the basis of polyurethane.

18. The vertebral column implant according to claim 15, wherein the elastic connecting element has a structure with one or more hollow spaces.

19. The vertebral column implant according to claim 18, wherein the elastic connecting element has a tubular cross-section with a wall thickness variable along the connecting element, the wall thickness conferring a desired variable stiffness upon the connecting element according to a position.

20. The vertebral column implant according to claim 15, wherein a screwhead of the bone screw has a slot so that the connecting element is inserted and anchored in the seat with elastic deformation.

21. The vertebral column implant according to claim 20, wherein grooves on the connecting element have a pitch, the seat on the screwhead has grooves with a same pitch and thus acts as a nut, so that the connecting element is screwed in and passed through the screwheads by rotation about the longitudinal axis.

22. The vertebral column implant according to claim 15, wherein the connecting element has a round cross-section with a flat side so that the connecting element is introduced into the seat with a reduced inside width and thereafter anchored by a rotation.

23. The vertebral column implant according to claim 15, wherein the connecting element has a round cross-section with two parallel flat sides so that the connecting element is introduced into the seat with a reduced inside width and thereafter anchored by a rotation.

24. The vertebral column implant according to claim 15, wherein the connecting element has a hollow space about the longitudinal axis, the hollow space facilitating elastic deformation for introduction into the seat.

25. The vertebral column implant according to claim 24, further comprising a plug pushed into the hollow space after introduction of the connecting element into the seat.

26. The vertebral column implant according to claim 15, wherein a screwhead of the bone screw is clampable, and the connecting element is clamped after introduction.

* * * * *